US00PP10145P

United States Patent [19]

van Andel

[11] Patent Number: Plant 10,145

[45] Date of Patent: Dec. 9, 1997

[54] ALSTROEMERIA PLANT VARIETY NAMED 'STAMIAL'

[75] Inventor: Jacob van Andel, Aalsmeer, Netherlands

[73] Assignee: Van Staaveren b.v., Netherlands

[21] Appl. No.: 629,924

[22] Filed: Apr. 10, 1996

[51] Int. Cl.[6] ..... A01H 5/00

[52] U.S. Cl. ..... Plt./87.1

[58] Field of Search ..... Plt./87.1

[56] References Cited

U.S. PATENT DOCUMENTS

P.P. 7,816 3/1992 Carrier ..... Plt./87.1

*Primary Examiner*—James R. Feyrer

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 50B1200-01 and as pollen parent an unreleased, unpatented seedling identified as 50B300-01 from among my collection of Alstroemeria seedlings maintained under on controlled conditions in a greenhouse at Van Staaveren B.V., Aalsmeer, The Netherlands, for developmental purposes. The varietal denomination of the new variety is 'Stamial'.

The first act of asexual reproduction of 'Stamial' was in Aalsmer, The Netherlands, by propagation by dividing rootstocks. Asexual reproduction through successive generations has demonstrated that the combination of characteristics as herein disclosed for 'Stamial' are firmly fixed and retained through successive generations of asexual reproduction.

'Stamial' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stamial' are characterized by flowers of unusual coloration, as described herein. The plant blooms profusely with annual production, including production of flower stems in spring and fall under greenhouse conditions in The Netherlands, which is desirable characteristic in a cut flower variety. The flower-bearing stems are of excellent quality. 'Stamial' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Amaryllidaceae.
- *Genus.*—Alstroemeria sp.
- *Commercial.*—Alstroemeria hybrid.

Origin: Seedling.

PLANT

Form: Bush.
Shape: Upright.
Height: About 130 to 160 cm.
Main stem or cane length: About 140 cm.
Growth: Vigorous.
Strength: Strong.
Foliage:
- *Quantity.*—Abundant.
- *Number of leaves.*—About 25 to 30 per stem.
- *Size of leaf.*—Length: About 10 to 15 cm. Width: About 2 to 3 cm.
- *Shape of leaf.*—Elliptical.
- *Margin type.*—Straight.
- *Texture.*—Glossy.
- *Color.*—Upper side: Near 137A. Underside: Near 137C.
- *Rhizomes.*—Yes. Color: Near 155D. Size: About 10–30 cm.

INFLORESCENCE—FLOWER

Blooming habit: Recurrent.
Blooms Profusely.
- *Spring.*—Yes.
- *Fall.*—Yes.
- *Has tendency to give few blooms in fall.*—No.

Size: Small.
- *Diameter.*—About 3 cm.
- *Depth.*—About 4 cm.

Borne: Progressively along simple racemes.
Shape or form:
- *When bloom first opens.*—Funnel form.
- *When bloom matures.*—Funnel form.

Petalage:
- *Number of petals.*—6.
- *Arrangement.*—Two concentric circles of 3 petals.

Production: Good annual production, including production of flower stems in spring and fall under greenhouse conditions in The Netherlands.

*Form.*—Obovate.

*Margin type.*—Minutely crimped.

*Apex.*—Outer petals broadly cuspidate; green points, and, inner petals narrowly cuspidate with small, white points.

*How long do petals stay on stem?.*—About 3 weeks.

*Texture.*—Soft.

*Appearance.*—Velvety.

*Color (summer/fall).*—Outer petal/floret: Body near 62A to 62B; base near 155D; reverse side near 62A; no stripes; distinct central spot, near 62A, which appears at the top surface of the petals. Inside lateral petal: Apical, marginal portions are red-purple, near 62B which is bordered by a narrow white band. the narrow white band suffuses to bright yellow, near 12A. The bright yellow, which is predominant in the central portions of the these petals, bleeds gradually to near white at the base. From about 40 to 50 stripes, near 187A, are presented in a pattern over the length of these petals. The color patterns and shadings of the reverse sides follow those of the top surface. Inside median petal: Body near 62B; base near 155D; reverse near 62B; range of stripes in the inside median petal is 5 to 30 stripes, near 187A, per petal.

Peduncle or flower stem:

*Length.*—About 3 to 6 cm.

*Color.*—Near 137B to 137C.

*Strength.*—Strong.

*Upright.*—Yes.

Discoloration after full bloom? Slightly.

Is bloom affected by wet or hot weather? No.

Persisence (does flower hang on and dry?): No.

Disease resistance: Unknown.

Fragrance: None.

Lasting quality:

*On plant.*—About 3 weeks.

*As cut flower.*—About 14 days.

BUD

Size:

*Diameter.*—About 6 to 15 mm.

*Depth or length.*—About 1 to 2 cm.

Form or shape: Pear-shaped.

*Long.*—About 1 to 2 cm.

*Pointed.*—No.

Rate of opening: Fast.

Color of petals/florets:

*When petals begin to unfurl.*—Near 63B.

REPRODUCTIVE ORGANS

Stamen:

*Number.*—6.

*Arrangement.*—Around the style.

Anthers:

*Size.*—About 6 to 8 mm.

*Color.*—Near 165C.

Filaments:

*Length.*—About 4 to 5 cm.

*Color.*—Near 155D.

Pollen:

*Color.*—Copious in quantity and gray, near 198B, in coloration.

Pistils:

*Number.*—1.

Styles:

*Length.*—About 4 to 5 cm.

*Color.*—Near 155D.

Stigmas:

*Color.*—Near 155D.

FRUIT

Fertile: No.

Shape: Capsular, but no seeds present.

Color at maturity: Near 163A.

I claim:

1. A new variety of Alstroemeria plant, substantially as herein shown and described.

* * * * *

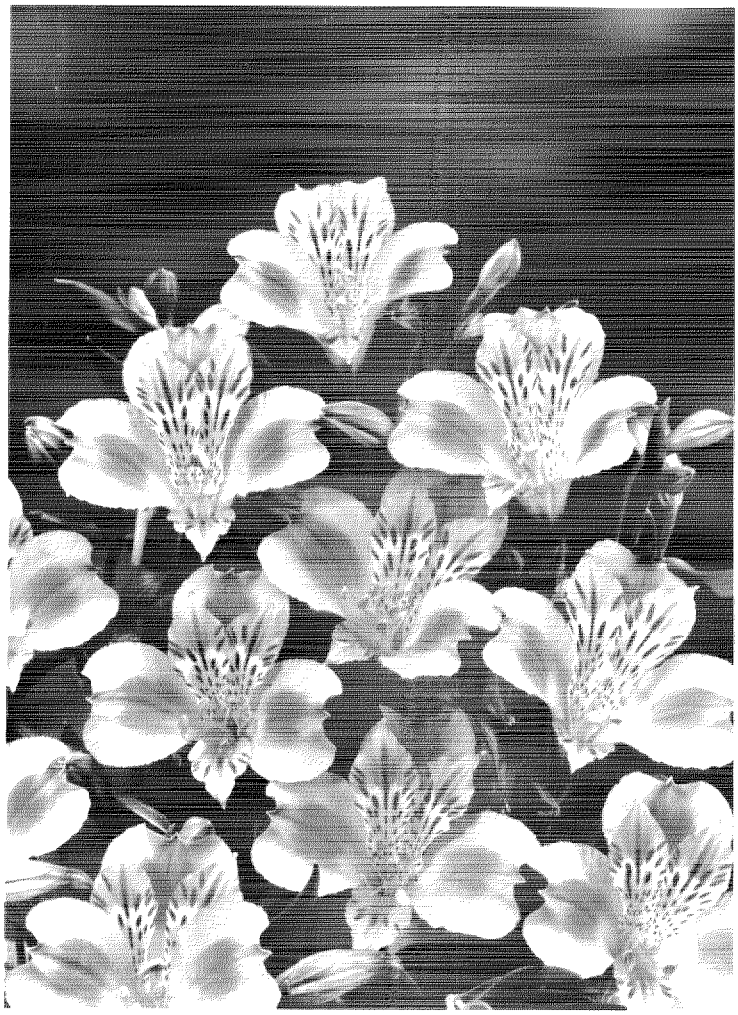

UNITED STATES PATENT AND TRADEMARK OFFICE

CERTIFICATE OF CORRECTION

PATENT NO. : Plant 10,145
DATED : December 9, 1997
INVENTOR(S) : Jacob van Andel It is certified that error appears in the above-indentified patent and that said Letters Patent is hereby corrected as shown below:

Column 1, line 8, after "under" delete "on".
Column 1, line 13, replace "Aalsmer" with -- Aalsmeer --.
Column 3, line 35, replace "Persisence" with -- Persistence --.

Signed and Sealed this

Eighth Day of December, 1998

*Attest:*

*Attesting Officer*

BRUCE LEHMAN

*Commissioner of Patents and Trademarks*